(12) United States Patent
Jacobson et al.

(10) Patent No.: US 6,464,992 B2
(45) Date of Patent: Oct. 15, 2002

(54) TOPICAL MICRONUTRIENT DELIVERY SYSTEM AND USES THEREOF

(75) Inventors: Elaine L. Jacobson, Tucson, AZ (US); Myron K. Jacobson, Tucson, AZ (US); Jaber G. Qasem, Tucson, AZ (US); Hyuntae Kim, Tucson, AZ (US); Moonsun Kim, Tucson, AZ (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 09/832,571

(22) Filed: Apr. 11, 2001

(65) Prior Publication Data

US 2002/0037898 A1 Mar. 28, 2002

Related U.S. Application Data

(60) Provisional application No. 60/197,828, filed on Apr. 14, 2000.

(51) Int. Cl.$^7$ .................. A61K 7/44; A61K 7/48; A61F 2/02; A61F 13/02; A61L 15/16
(52) U.S. Cl. .................. 424/401; 424/78.03; 424/423; 424/433; 424/436; 424/447; 424/449
(58) Field of Search .................. 424/401, 449, 424/78.03, 433, 436, 447, 423

(56) References Cited

U.S. PATENT DOCUMENTS 5,185,325 A * 2/1993 Brawn et al. .................. 514/23

* cited by examiner

Primary Examiner—Carlos Azpuru
(74) Attorney, Agent, or Firm—Fulbright & Jaworski LLP.

(57) ABSTRACT

The invention involves methods and compositions useful in delivering micronutrients to cells. By formulating the micronutrient in the form of an ester that is convertible to the active form of the micronutrient, one can combine it with a co-ester that inhibits esterases, so that the micronutrient can reach the targeted cells prior to degradation. Both methods and compositions are described.

48 Claims, 3 Drawing Sheets

TOPICAL MICRONUTRIENT DELIVERY SYSTEM AND USES THEREOF

PRIORITY CLAIM

This application claims priority to provisional application No. 60/197,828 filed Apr. 14, 2000, incorporated by reference in its entirety.

FIELD OF THE INVENTION

This invention relates to a topical micronutrient delivery system. The system is useful in, e.g., delivery of desirable and/or necessary materials, such as micronutrients, to a subject in need of same. Therapeutic uses of the system are also described.

BACKGROUND AND PRIOR ART

The skin plays multiple roles in protection from environmental insults. Environmental exposure results in the progressive deterioration of skin that is initially cosmetic but can lead to end stage diseases such as actinic keratosis and skin cancer.

Skin deterioration results from damage to DNA and protein, and compelling evidence indicates that reactive oxygen species ("ROS" hereafter) are involved in the generation of DNA damage that results in the loss of genomic integrity of skin cells. Skin cells contain inherent mechanisms for the maintenance of genomic integrity. A growing body of evidence demonstrates that micronutrients including vitamins B6, B12, C, E, folate, and niacin are involved in the maintenance of genomic integrity via mechanisms ranging from scavenging ROS, to the repair of DNA damage. Sub-clinical micronutrient deficiencies are prevalent even in advanced societies and micronutrient status decreases with age.

Skin is a complex organ system, consisting of multiple layers. The uppermost, or "stratum corneum" layer consists of non-living material derived primarily from the terminal differentiation of epidermal keratinocytes, and provides a protective barrier for the underlying components of skin. The epidermis contains a number of cell types, although keratinocytes are the major cell type. Dermal fibroblasts are embedded within a matrix comprised of collagen, elastin, proteoglycans, and other extracellular matrix molecules. Blood capillaries are found in the dermis, but the epidermis is non-vascular.

As people age, progressively deleterious changes in skin appearance occur. The initial changes are the loss of smooth skin texture and the appearance of age spots, followed by changes in elasticity that lead to the appearance of skin wrinkles. The age at which these changes appear and the rate at which one stage progresses to the next varies greatly from individual to individual. During the normal aging process, both the epidermis and dermis become thinner, with a loss of cell number and connective tissue, leading to the appearance of fine wrinkles. Ultraviolet (UV) irradiation from the sun causes photodamage that accelerates skin deterioration. In contrast to the thinning observed in sun-protected skin, photodamaged skin has a thickened and rough appearance with an increase in deeper skin wrinkling. Photodamage also causes end-stage skin deterioration, including pre-malignant lesions termed actinic keratosis, and skin cancer.

Compelling evidence now indicates that oxidative stress, defined as an abnormal accumulation of ROS, is involved in the pathophysiology of skin deterioration. ROS include superoxides, the hydroxyl radical, hydrogen peroxide, singlet oxygen, nitric oxide, peroxynitrite, and hypochlorite. See, e.g., Simonian, et al., Ann. Rev. Pharmacol. Toxicol. 36:83–106 (1996), incorporated by reference. All cells are exposed to ROS during the normal course of energy metabolism, via environmental exposure and/or immune surveillance. While ROS are involved in normal cell signaling pathways, elevation of ROS during oxidative stress disrupts signaling pathways, often resulting in cell death by apoptosis or necrosis. Thus, it is likely that ROS are involved in the loss of cell numbers observed even in sun-protected skin over time. Exposure to the ultraviolet rays of sunlight is a major source of skin oxidative stress. Two major targets for damage by ROS in skin are DNA and protein. DNA damage is of particular interest in that unrepaired damage can lead to the loss of skin cells and to an altered function of cells that survive genotoxic stress.

While some changes in skin during aging can not be avoided, much of the skin deterioration that occurs at an early age is avoidable. Skin cells contain a number of protective mechanisms for the prevention and repair of damage to DNA and proteins caused by ROS. First, a number of intracellular molecules, including glutathione and the antioxidant vitamins C and E, play key roles in scavenging ROS before they can react with cellular macromolecules. Indeed, the antioxidant vitamins have already found application in the prevention of skin deterioration, as they are components of many skin creams. Second, cells contain complex mechanisms for the maintenance of genomic integrity. Of particular interest herein is the accumulating evidence for the involvement of micronutrients in maintenance of DNA structure and in DNA repair mechanisms. There are approximately 40 micronutrients that are required, in small amounts, to maintain normal human metabolism (Ames, Ann. N.Y. Acad. Sci 889: 87–106 (1999), incorporated by reference). For many of these micronutrients, a sizeable portion of the population consumes significantly less of the micronutrient than what has been established as the recommended daily intake see Wilson, et al. Data Tables: Combined Results from USDA's 1994 and 1995 continuing survey of food intakes by individuals and 1994 and 1995 diet and health knowledge survey (USDA/ARS Food Surveys Research Group, Beltsville Human Nutrition Research Center, Riverdale, Md. (1997), incorporated by reference. The percentage of the U.S. population that is deficient in a particular micronutrient ranges from 2 to 20%. Ames, supra. To complicate matters, micronutrient status deteriorates further with increasing age. Bates, et al., Br. J. Nutr 82(1):7–15 (1999). Much of our knowledge about the relationship between micronutrients and various diseases such as cancer derives from measurements of micronutrient levels in plasma. While there is much to learn regarding plasma micronutrient levels and target tissue levels, there is evidence that deficiencies observed in plasma are also observed in skin. See Peng, et al., Canc. Epidermiol Biomarkers Prev 2(2): 145–50 (1993). This is not surprising, since the epidermal layer of skin does not contain blood vessels, making delivery of dietary micronutrients to skin inefficient. Of particular concern for skin deterioration are observations that micronutrient deficiencies can mimic radiation- and chemical-induced DNA damage, by effecting single-and double-strand breaks and/or oxidative lesions. Ames, supra. Specifically, deficiencies in folic acid, B12, B6, niacin, vitamin C, vitamin E, iron, and zinc can result in DNA damage. Ames, supra. For each of these micronutrients, there are known metabolic pathways that describe the rationale by which a deficiency results in DNA damage in the absence of genotoxic stress. Additionally, the micronutrient deficiencies would be expected to exacerbate the deleterious effects of genotoxic stress. The above information indicates that improving the micronutrient status of skin cells is desirable, as this will improve the health of skin and likely retard skin deterioration.

It is an object of the invention to provide a tropical delivery system which is useful in making micronutrients available, or making these micronutrients available in greater quantities than possible in the past.

It is a further object of the invention to arrest or to prevent deterioration of organs such as skin, by making micronutrients available in amounts sufficient to arrest or to prevent the deterioration.

How this is accomplished will be seen from the disclosure which follows.

DETAILED DESCRIPTION OF PREFERRED EMBODIMENTS

Figure 1:
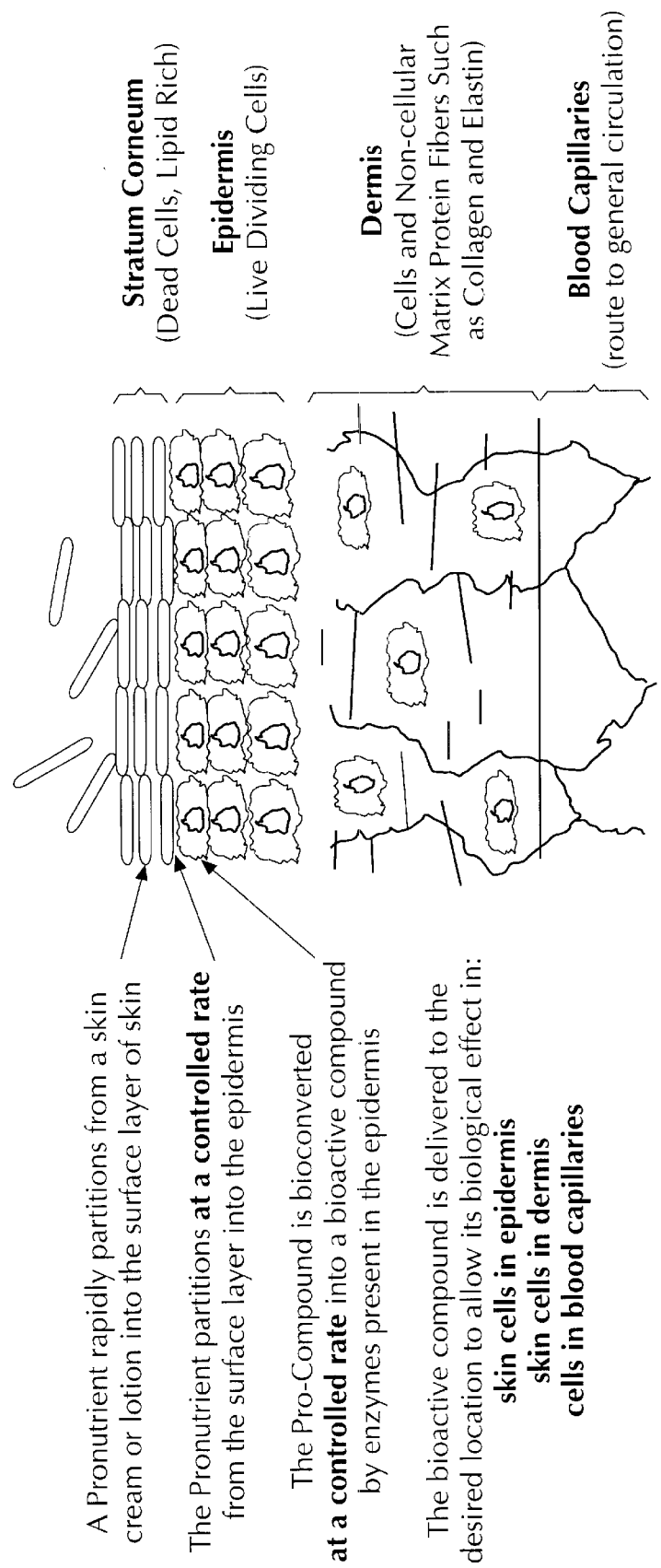
FIG. 1 depicts the skin, in cross section, in combination with an illustration of the delivery system of the invention.
Figure 2:
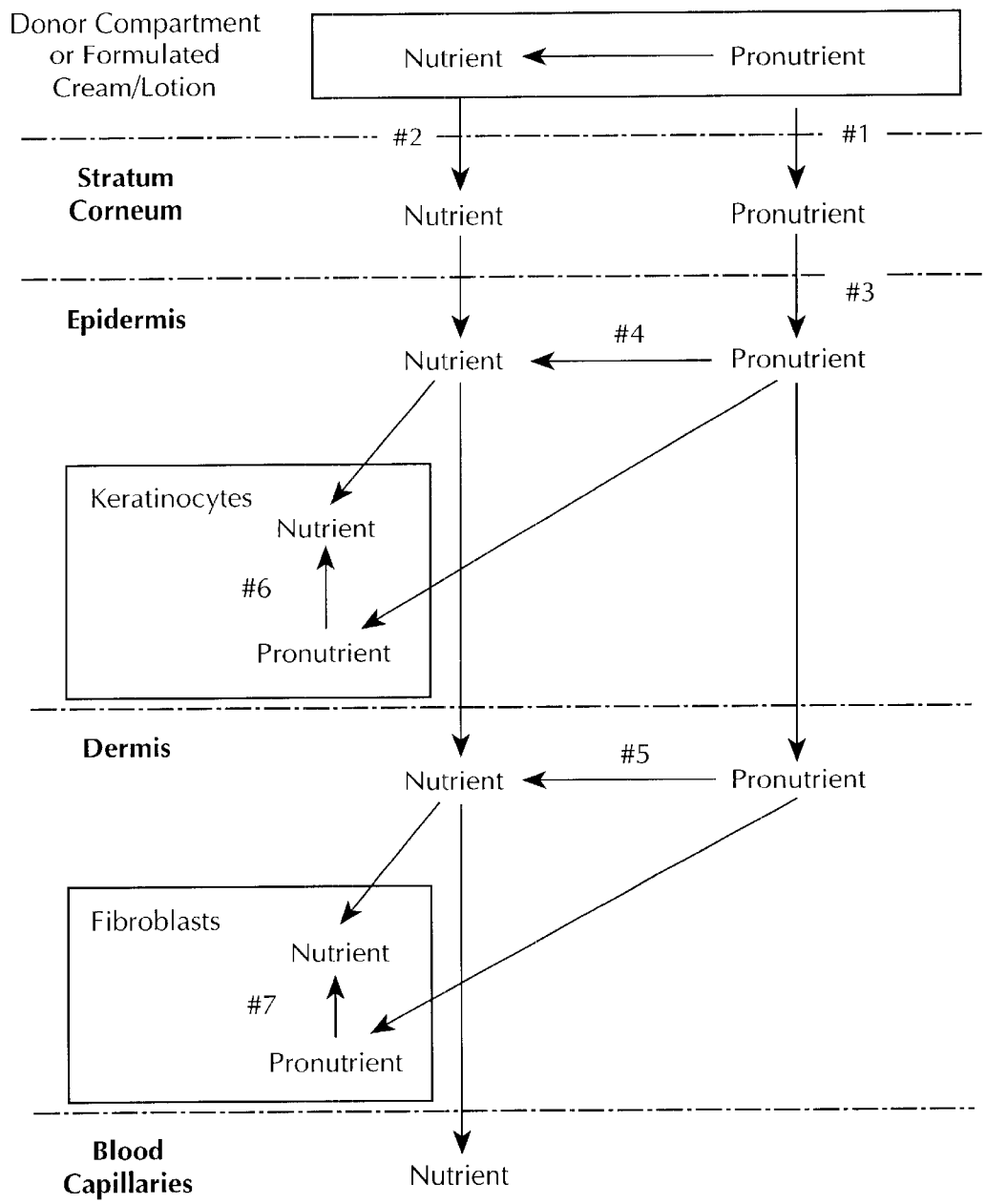
FIG. 2 elaborates an embodiment of the invention.

The topical delivery system of the invention takes into consideration the two distinct barriers that influence the delivery of micronutrients to skin, i.e., the lipophilicity of stratum corneum, and skin metabolic activity. The micronutrient delivery system of the invention is outlined in FIG. 1. In brief, the partitioning of the micronutrient in and out of the stratum corneum is controlled by the nutrient esters with optimal lipophilicity for such partitioning. These are described, infra. The term "pronutrient" is used to describe these compounds. Further, the rate and site of inetabolic conversion of pronutrients is controlled by the use of inactive companion co-esters as described infra. Several features are required for this delivery system to function optimally. FIG. 2 shows a multiple compartment model that served as the framework for the development of these criteria. The model micronutrient used is niacin, but the skilled artisan will realize that the information disclosed is relevant to a wide variety of micronutrients as described in more detail infra.

The highly lipophilic nature of the stratum corneum dictates that the desired micronutrient must be sufficiently lipophilic to effectively partition into the stratum corneum from the donor compartment, which may be a skin cream or lotion (#1 in FIG. 2). This necessitates the preparation of distinct lipophilic pronutrients, as most micronutrients of interest are too hydrophilic to meet this criterion. As described in more detail infra, the required lipophilicity needed for diffusion from the stratum corneum into the epidermis predict that efficacious pronutrients should be sufficiently lipophilic to rapidly partition from the cream or lotion into the stratum corneum. Esters of micronutrients are used herein, as this allows lipophilic derivatives to be prepared and also allows their efficient bioconversion following diffusion out of the stratum corneum into the epidermis.

The lipophilicity of the pronutrients should allow them to be formulated in, e.g., skin creams or lotions, and the ester linkages should be very stable in these formulations. Although the non-derivatized micronutrient would be expected to partition very slowly into the stratum corneum (#2 in FIG. 2), a pronutrient that is very stable is high desirable. The esters disclosed herein are pronutrients that are stable to chemical hydrolysis under aqueous conditions, as well when formulated in a cream or lotion.

The pronutrient must partition into the epidermis at a relatively slow rate to achieve sustained delivery to the cellular components of skin with minimal systemic delivery (#3 in FIG. 2). A correlation between skin permeability ($P_B$) and the physicochemical properties of the drug, such as octanol/water partition coefficient ($P_{oct/w}$) are of value in predicting drug transport across skin. A linear correlation between skin permeability (Log $P_B$) of many compounds and their logarithm of $P_{oct/w}$ has been established and is well know in the art. Deviations from this relationship are observed for very hydrophilic and extremely lipophilic compounds. Compounds with optimal lipophilicity for delivery of a micronutrient to the cellular components of skin are disclosed herein. For niacin, e.g., as the model micronutrient, a series of alkyl esters of niacin were prepared and their relative lipophilicity was determined. Next, the efficacy of these pronutrients in delivering niacin to the cellular components of skin by measuring the bioactive form of niacin (NAD) following topical application thereof, using established models.

It is believed that short chain esters may have an intrinsic flux from the stratum corneum that is too rapid for sustained delivery to skin, i.e., systemic delivery will be favored. Likewise, a very long chain derivative is predicted to have a lipophilicity that will have an intrinsic flux that is too slow for effective delivery. The lipophilicity of a number of new niacin esters disclosed in Ser. No. 09/452,617, along with some commercially available esters is shown in Table 1 infra, together with values for the two, unmodified molecules, i.e., nicotinic acid and nicotinamide. The lipophilicity is reported as log P values, where P refers to the octanol/water partition coefficient, described supra. Table 1 also shows that nicotinic acid and niacin esters with log P values of less than 6 cause vasodilation at the site of topical application. This demonstrates that these nicotinic acid and niacin esters are delivering niacin at a rate that exceeds the minimum concentration needed to cause vasodilation of the endothelial cells of the blood capillaries. Niacin esters with log P values greater than 6 do not cause dilation. Nicotinamide does not cause vasodilation, but its log P value also predicts that it will deliver nutrient too rapidly to allow the cellular components of skin to assimilate it and convert it to its bioactive form NAD. To determine the optimum physical properties of pronutrient for topical delivery to the cells of the skin, niacin esters with log P values ranging from 6.6 to 9.2 were examined by determination of the active form of niacin, NAD in the skin following application of the lotion. Results from a typical experiment are shown in Table 2, where niacin pronutrients formulated at 1% were topically applied to the backs of hairless mice once a per day for three days. After three days, skin was removed from both the site of application and from the abdomen of each animal, and the NAD content was analyzed. Analysis of skin from the backs of the animals demonstrated that niacin esters of 12, 14, and 16 carbons resulted in an increased NAD content, although the 14 carbon ester was the most effective. In further experiments, it was determined that a niacin ester with a carbon side chain of 18, and a log P value of 9.7 was less effective that the ester with a 16 carbon side chain. Further, it was shown that topical application of niccotinamide, which has a log P value of −0.34, had no effect on skin cell NAD content. The results of Table 2 also show that the delivery was topical for the 14 and 16 carbon esters, as there was no increase in the NAD content of the abdomen where the pronutrient was not applied. Topical application of the 12 carbon ester did show some delivery to the abdomen, which is consistent with the suggestion, supra that this compound should have the fastest rate of delivery of the compounds compared in this experiment.

The delivery approach disclosed herein involves the bioconversion of the pronutrient to the desired micronutrient by the action of skin esterases. Studies on the esterase distribution of skin have shown that the stratum corneum has little or no activity, the epidermis has the highest activity and the dermis has reduced activity relative to the epidermis. See Sugibayashi, et al. J. Controlled Release 62:201–208 (1999)

incorporated by reference. Delivery should be possible whether the bioconversion is extracellular (#4 & 5, FIG. 2) or following uptake by the target cells (#6 & 7 in FIG. 2) as cells contain specific transport systems for micronutrients and the lipophilicity of the pronutrients should make them readily bioavailable via passive diffusion. Since the stratum corneum contains little or no esterase activity, the rate of disappearance of a pronutrient from the stratum corneum depends only on the rate of diffusion, which can be described by Fick's second law of diffusion:

$$dC_{SC}/dt = D_{SC} d^2 C_{SC}/d^2 x$$

where dc/dt is the change in pronutrient concentration over time, $C_{SC}$ is the pronutrient concentration in the stratum corneum and $D_{SC}$ is the diffusion coefficient from the stratum corneum.

In the epidermis and dermis, where both diffusion and metabolism are occurring simultaneously, both diffusion and metabolism must be considered. Thus the rate of disappearance from these compartments can be described by:

$$dC_{proN}/dt = D_{proN} d^2 C_{proN}/d^2 x - V_{max}(x) \cdot C_{proN}/K_m + C_{proN}$$

where $C_{proN}$ and $D_{proN}$ are the concentration and diffusion co-efficient of the pronutrient in the epidermis or dermis and $V_{max}(x)$ is maximum rate of metabolic conversion at position x, and $K_m$ is the Michaelis-Menten constant.

The use of ester derivatives of micronutrients is applicable to a wide range of micronutrients, some of which are presented in Table 3. The micronutrients shown contain either an acid functionality, an alcohol functionality, or both. Micronutrients containing an acid functional group can be esterified to a long chain alcohol to allow formation of the desired lipophilicity for topical delivery. Micronutrients with an alcohol functionality can be esterified to a long chain acid to achieve the desired lipophilicity.

Figure 3:
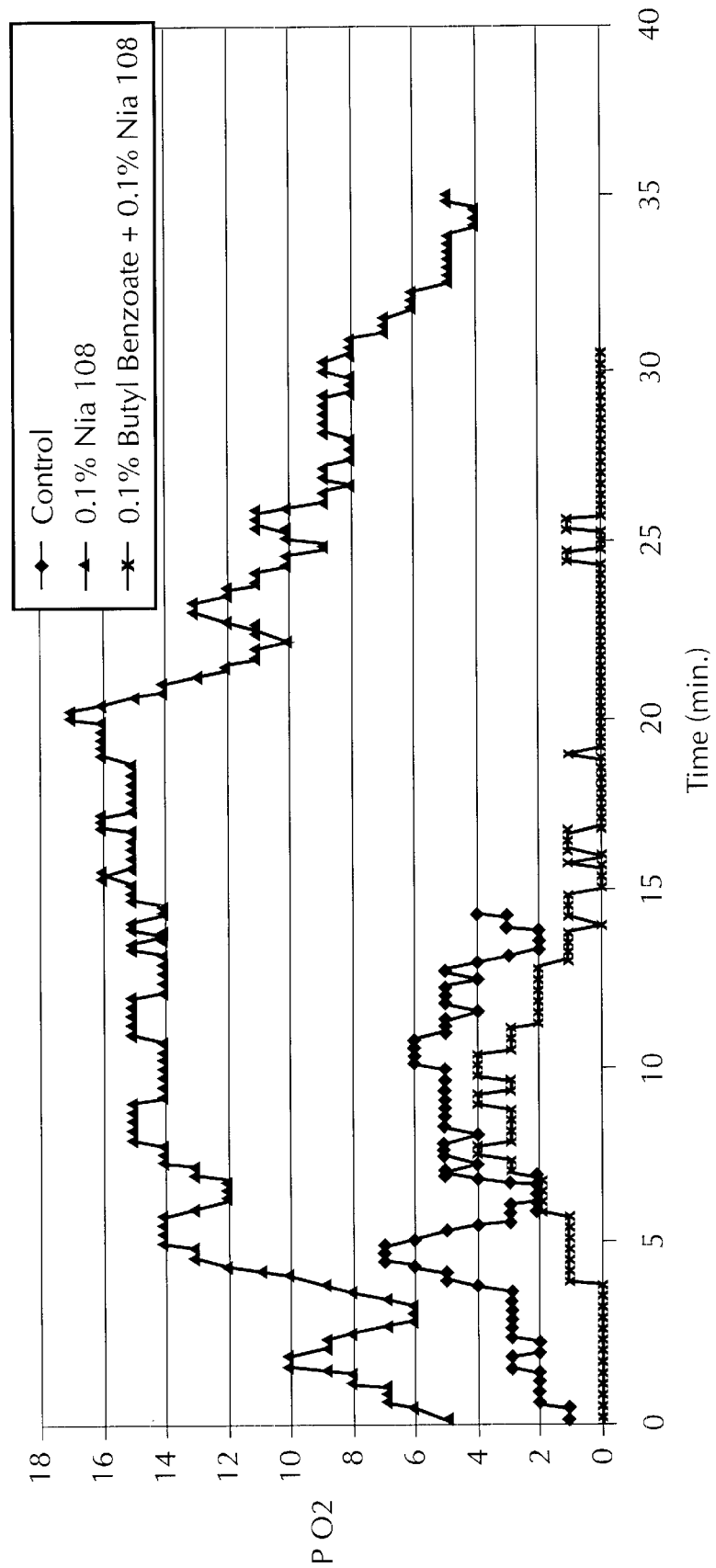
FIG. 3 outlines the results of an experiment designed to determine the efficacy of co-esters in modulating delivery of active compounds.

It is preferred to combine the esters described supra, with inactive co-esters, as these allow modulation of nutrient delivery to specific locations within skin. The high esterase content in the epidermis favors the delivery of topically applied pronutrients to cells present in the epidermis. While delivery to cells in the epidermis is a major goal of the topical delivery system, it is also highly desirable to achieve delivery to dermal fibroblasts and to endothelial cells in blood capillaries in the skin. Enhancing delivery to the dermis and blood capillaries can be achieved by the use of inactive co-esters that can be used to modulate the extent of bioconversion of pronutrients in the epidermis. For co-esters to modulate the rate of conversion of pronutrients in the skin, two criteria must be met. First, the co-ester must have lipophilicity similar to that of the pronutrient, such that flux from the stratum corneum of the pronutrient and co-ester is similar. Second, the co-ester must effectively compete with the pronutrient for bioconversion by the skin esterases. At concentrations of pronutrient below enzyme saturation, co-esters will competitively inhibit the metabolic conversion in the epidermis (#4 in FIG. 2) and allow the pronutrient to pass intact to the dermis (#5 in FIG. 2) for conversion and delivery. This approach minimizes the required dose of pronutrients and provides a good targeted delivery system to the dermis. The targets of delivery in the dermis include both dermal fibroblasts and capillary endothelial cells. For the dermal fibroblasts, the aim is to deliver niacin for conversion to AND. For the capillary endothelial cells, the known vasodilation properties of niacin may be useful for increasing blood flow in the dermis, increasing the supply of oxygen and other essential nutrients and increasing the efficiency of removal of carbon dioxide and other metabolic end products. An experiment demonstrating the use of co-esters to modulate delivery is shown in FIG. 3. For this experiment, the eight carbon ester of niacin (octyl nicotinate) for delivery of niacin to the endothelial cells of blood capillaries, in order to increase the oxygen content of skin. In this experiment, a transcutaneous oxygen monitor has been used to determine oxygen content in the skin. A lotion containing the test compound was topically applied for thirty minutes. The lotion was then removed and the transcutaneous oxygen monitor was placed on the surface of the skin. The control experiment showed that the oxygen content of skin ($PO_2$) shows a value of 4 mm, demonstrating the relatively low oxygen content was increased. The duration of the increase is not long because the lotion must be removed in order to make the oxygen measurement. Butyl benzoate was chosen as the co-ester. Butyl benzoate has a log P value of 3.5 compared to a log P value of 4.8 for octyl nicotinate. FIG. 3 shows that a formulation containing both octyl nicotinate and butyl benzoate blocked the increase in skin oxygen content elicited by octyl nicotinate alone, demonstrating modulation of delivery of the pronutrient by the co-ester.

The experiments which follow set forth the invention in greater detail, but should not be construed as limiting the invention in any way.

EXAMPLE 1

Nicotinic acid esters were synthesized in accordance with Ser. No. 09/452,617, filed Dec. 1, 1999, incorporated by reference. In brief, nicotinoyl chloride was combined with triethylamine (TEA), dimethylaminopyridine (DMAP), and various alkyl alcohols, under nitrogen. Esters resulting from the synthesis were separated via silica gel column chromatography, and converted to HCl salts for further purification, using standard methods. The purity was confirmed via thin layer chromatography, and 1H-NMR.

The $P_{oct/w}$ values for these compounds were determined in accordance with Harnisch, et al., J. Chromatog. 282:315–332 (1983), incorporated by reference. In brief, this HPLC method determines capacity factor ("K'") for each pronutrient, and also establishes a linear relationship between the logarithm of $P_{oct/w}$ and the logarithm of K', for short chain pronutrients. Rate of hydrolysis of candidate nicotinic acid ester derivatives was determined, in aqueous phosphate buffer, at physiological pH (7.4), with incubation at 37° C. Rate of pronutrient disappearance from solution was monitored, by HPLC, at 254 nm.

EXAMPLE 2

In animal experiments, female hairless mice (HRS-J, 6–8 weeks old), received daily topical application of nicotinic acid esters, using 200 mg of commercially available "Vanicream" lotion, at a 1.0% (wt/wt) concentration, for three days. Control animals received Vanicream only. The lotions were applied, daily, for one week.

Animals were euthanized, and dorsal and ventral skin samples were then frozen in liquid nitrogen, and stored at −80° C. In order to analyze NAD and protein content, tissue samples were homogenized, in 0.5M, ice cold $HClO_4$, and then centrifuged at 3000 rpm for 15 minutes. The resulting supernatants were neutralized with ice-cold 2M KOH/0.66M $KH_2PO_4$, in order to determine NAD. The NAD was determined in accordance with Jacobson, et al., Meth. Enzymol. 280: 221–230 (1997) incorporated by reference, while a commercially available BCA method was used for protein determination.

TABLE 1

Properties of Niacin Pronutrients

| Alkyl Carbon Chain Length | Log P Value | Erythematous Response |
|---|---|---|
| Nicotinamide (No side chain) | −0.34 | No |
| Nicotinic Acid (No side chain) | −0.46 | Yes |
| 1 carbon | 0.84 | Yes |
| 2 carbons | 1.3 | Yes |
| 4 carbons | 2.4 | Yes |
| 6 carbons | 3.5 | Yes |
| 8 carbons | 4.8 | Yes |
| 10 carbons | 5.8 | Slight |
| 12 carbons | 6.6 | No |
| 13 carbons | 7.5 | No |
| 14 carbons | 7.6 | No |
| 15 carbons | 8.3 | No |
| 16 carbons | 9.2 | No |
| 18 carbons | 9.7 | No |

TABLE 2

Skin NAD content following topical application of niacin pronutrients

| | | Skin NAD content of back | | Skin NAD content of abdomen | |
|---|---|---|---|---|---|
| Alkyl Group | Log P | pmol NAD/mg tissue | % | pmol NAD/mg tissue | % |
| Lotion only | — | 91.4 +/− 18.4 | 100 | 60.4 +/− 15.2 | 100 |
| 12 Carbons | 6.6 | 129.4 +/− 15.4 | 141 | 82.6 +/− 14.8 | 137 |
| 14 Carbons | 7.6 | 165.7 +/− 12.0 | 181 | 55.8 +/− 13.8 | 92 |
| 16 Carbons | 9.2 | 109.5 +/− 8.3 | 120 | 52.1 +/− 10.4 | 86 |

TABLE 3

Micronutrient Candidates for Generation of Pronutrient Esters

| Contain Alcohol Group | Contain Carboxylic Acid Group |
|---|---|
| Vitamin B6 | Niacin |
| Folic Acid | Folic Acid |
| Vitamin B12 | Lipoic Acid |
| Pantothenic acid | Pantothenic acid |
| Carnitine | Carnitine |
| Riboflavin | |
| Ubiquinones | |

The foregoing sets forth the features of the invention, which relates, inter alia, to systems and methods for delivery of nutrients, such as micronutrients, to a subject. Preferably, these are topical delivery systems, in that they are formulated for administration in the same manner as are other topical formulations. In addition to creams and lotions, topical formulations such as shampoos, liquids such as eye washes, balms and sticks such as lip balms and deodorant sticks, mouthwashes and gavages, soaps, suppositories, patches, bandages, suturing threads, coated implant devices, and any other type of system designed for topical application are a part of the invention. Preferably, the formulation is designed for application to, e.g., skin or other organs, such as liver, lungs, stomach, etc., scalp, eyes, blood vessels, and so forth.

The micronutrient used in the formulations may be any of those referred to by Ames, et al., supra, such as those set out in table 3. Preferably, the micronutrient is one which contains an acid moiety (e.g., ascorbic acid), an alcohol moiety, or both. It is also preferred that the alcohol moiety or moieties of the micronutrient be in esterified form. These esterified forms of micronutrients should have a log P value ranging from about 6.5 to about 8.5, more preferably from about 7.0 to about 8.0. As was shown in the examples set forth herein, in the case of the niacin esters, a log P of about 7.6 was ideal. For niacin this resulted from an ester with a 14 carbon side chain. It will be understood by the skilled artisan that the preferred structures will vary from nutrient to nutrient or micronutrient to micronutrient, but the log P values will control. The computation of log P values should be carried out as described herein. The log P values recited herein are predictive of the rate of partitioning of the materials of interest. Many micronutrients of interest exist in esterified form. Processes for esterifying others are known to the art, and need not be set forth here.

As indicated, supra, it is preferred that the micronutrient of interest be combined with a "co-ester." This co-ester, as used herein, refers to a compound which is an ester, and is less lipophilic than the micronutrient, so that it will migrate slightly faster from, e.g., the stratum corneum so as to occupy esterases, such as skin esterases, thereby permitting diffusion of the micronutrient into the lower layers of the skin. In quantitative terms, it is preferred that the lipophilicity of the co-ester should be within a factor of about 20, i.e., have a log P which differs from the value for the micronutrient with which it is coadministered or formulated by from about 0.5 to about 1.5, preferably by about 1.0 to about 1.5.

Formulations as described above are covered by the invention, as are methods for delivering a micronutrient to a subject, via administering a combination of the micronutrient and the co-ester, in an amount sufficient to facilitate delivery of said micronutrient. In practice, the delivery system described herein can be administered to a site of injury, thus being used therapeutically, and/or it can be administered prophylactically, i.e., prior to exposure of the skin and/or organ to insult, genotoxic stress, etc. The formulations can be prepared such that they vary in strength. The concentration should range from about 0.005% to about 5.0%, more preferably from about 0.005% to 2.5%, and most preferably from about 0.01% to about 1.0% by weight of said applied composition.

Other features of the invention will be clear to the skilled artisan and need not be set forth herein.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. A method for delivering a nutrient to a subject, comprising topically applying to said subject a composition which comprises said nutrient, in the form of an ester, and a co-ester which inhibits esterases and is less lipophilic than the ester form of said micronutrient, in an amount sufficient to facilitate delivery of said nutrient to cells of said subject.

2. The method of claim 1, wherein said nutrient is a micronutrient.

3. The method of claim 2, wherein said micronutrient is a micronutrient which contains an alcohol group.

4. The method of claim 3, wherein said micronutrient is vitamin B6, folic acid, vitamin B12, pantothenic acid, carnitine, riboflavin or an ubiquinone.

5. The method of claim 2, wherein said micronutrient is a micronutrient which contains a carboxylic acid group.

6. The method of claim 5, wherein said micronutrient is ascorbic acid, niacin, folic acid, lipoic acid, pantothenic acid, or carnitine.

7. The method of claim 6, wherein said micronutrient is niacin.

8. The method of claim 7, wherein said niacin is administered in the form of an ester having an alkyl side chain of from 12–16 carbon atoms.

9. The method of claim 8, wherein said alkyl side chain consists of 14 carbon atoms.

10. The method of claim 1, wherein said co-ester has a lipophilicity log P value which differs from said micronutrient from about 0.5 to about 1.5.

11. The method of claim 1, wherein said ester and co-ester have log P values which differ from each other by about 1.3.

12. The method of claim 1, wherein said ester has a log P value of from about 6.5 to about 8.5.

13. The method of claim 12, wherein said ester has a log P value of from about 7 to about 8.

14. The method of claim 1, wherein said composition is in the form of a cream, a lotion, a shampoo, an eye wash, a balm, a stick, a mouthwash, a gavage, a soap, a suppository, a bandage, a suturing thread or an implant device.

15. The method of claim 1, wherein said subject suffers from a deficiency of said micronutrient.

16. The method of claim 15, comprising administering said composition to a site of injury on said subject.

17. The method of claim 1, wherein said co-ester is butyl benzoate.

18. Composition useful in delivering a nutrient to a subject, comprising: (i) an esterified form of said nutrient and (ii) a co-ester which inhibits esterases wherein said co-ester is less lipophilic than the esterified form of said nutrient.

19. The composition of claim 18, wherein said nutrient is a micronutrient.

20. The composition of claim 18, in a form suitable for topical administration.

21. The composition of claim 19, wherein said micronutrient contains an alcohol group.

22. The composition of claim 19, wherein said micronutrient contains a carboxylic acid group.

23. The composition of claim 21, wherein said micronutrient is vitamin B6, folic acid vitamin B12, pantothenic acid, carnitine, riboflavin, or an ubiquinone.

24. The composition of claim 22, wherein said micronutrient is ascorbic acid, niacin, folic acid, lipoic acid, pantothenic acid, or carnitine.

25. The composition of claim 24, wherein said micronutrient is niacin.

26. The composition of claim 25, wherein said niacin is in the form of an ester having an alkyl side chain of from 12–16 carbon atoms.

27. The composition of claim 26, wherein said alkyl side chain consists of 14 carbon atoms.

28. The composition of claim 18, wherein said co-ester is benzyl benzoate.

29. The composition of claim 18, wherein (i) and (ii) have log P values which differ from each other by about 1.3.

30. The composition of claim 18, wherein (i) has a log P value of from about 6.5 to about 8.5.

31. The composition of claim 18, wherein (i) has a log P value of from about 7 to about 8.

32. A method for delivering a nutrient to a subject suffering from deficiency of said nutrient comprising topically applying to said subject a composition which comprises said nutrient, in the form of an ester, and a co-ester which inhibits esterases, in an amount sufficient to facilitate delivery of said nutrient to cells of said subject.

33. The method of claim 32, wherein said nutrient is a micronutrient.

34. The method of claim 33, wherein said micronutrient is a micronutrient which contains an alcohol group.

35. The method of claim 34, wherein said micronutrient is vitamin B6, folic acid, vitamin B12, pantothenic acid, carnitine, riboflavin or an ubiquinone.

36. The method of claim 33, wherein said micronutrient is a micronutrient which contains a carboxylic acid group.

37. The method of claim 36, wherein said micronutrient is ascorbic acid, niacin, folic acid, lipoic acid, pantothenic acid, or carnitine.

38. The method of claim 37, wherein said micronutrient is niacin.

39. The method of claim 38, wherein said niacin is administered in the form of an ester having an alkyl side chain of from 12–16 carbon atoms.

40. The method of claim 39, wherein said alkyl side chain consists of 14 carbon atoms.

41. The method of claim 32, wherein said co-ester is less liphophilic than the ester form of said micronutrient.

42. The method of claim 41, wherein said co-ester has a lipophilicity log P value which differs from said micronutrient from about 0.5 to about 1.5.

43. The method of claim 32, wherein said ester and co-ester have log P values which differ from each other by about 1.3.

44. The method of claim 32, wherein said ester has a log P value of from about 6.5 to about 8.5.

45. The method of claim 44, wherein said ester has a log P value of from about 7 to about 8.

46. The method of claim 32, wherein said composition is in the form of a cream, a lotion, a shampoo, an eye wash, a balm, a stick, a mouthwash, a gavage, a soap, a suppository, a bandage, a suturing thread or an implant device.

47. The method of claim 32, comprising administering said composition to a site of injury on said subject.

48. The method of claim 32, wherein said co-ester is butyl benzoate.

* * * * *

UNITED STATES PATENT AND TRADEMARK OFFICE
CERTIFICATE OF CORRECTION

PATENT NO. : 6,464,992 B2  Page 1 of 1
APPLICATION NO. : 09/832571
DATED : October 15, 2002
INVENTOR(S) : Elaine L. Jacobson et al.

It is certified that error appears in the above-identified patent and that said Letters Patent is hereby corrected as shown below:

Claim 1, line 5, change "mcironutrient" to --nutrient--.

Signed and Sealed this

Twenty-sixth Day of February, 2008

JON W. DUDAS
*Director of the United States Patent and Trademark Office*

UNITED STATES PATENT AND TRADEMARK OFFICE
CERTIFICATE OF CORRECTION

PATENT NO. : 6,464,992 B2  Page 1 of 1
APPLICATION NO. : 09/832571
DATED : October 15, 2002
INVENTOR(S) : Elaine L. Jacobson et al.

It is certified that error appears in the above-identified patent and that said Letters Patent is hereby corrected as shown below:

Column 8
Claim 1, line 66, change "mcironutrient" to --nutrient--.

This certificate supersedes the Certificate of Correction issued February 26, 2008.

Signed and Sealed this

Eighth Day of April, 2008

JON W. DUDAS
*Director of the United States Patent and Trademark Office*